United States Patent
Hughes

(10) Patent No.: US 6,256,818 B1
(45) Date of Patent: Jul. 10, 2001

(54) HEATED MASSAGE PILLOW

(76) Inventor: Angela Y. Hughes, 3507 Marconi Cove, Memphis, TN (US) 38118

( * ) Notice: Subject to any disclaimer, the term of this patent is extended or adjusted under 35 U.S.C. 154(b) by 0 days.

(21) Appl. No.: 09/405,706

(22) Filed: Sep. 24, 1999

(51) Int. Cl.$^7$ ............................................. A47G 9/00
(52) U.S. Cl. .................... 5/639; 5/636; 5/421; 5/490; 5/915
(58) Field of Search ................ 5/639, 636, 640, 5/421, 284, 694, 490, 915

(56) References Cited

U.S. PATENT DOCUMENTS

| | | | |
|---|---|---|---|
| 2,606,996 * | 8/1952 | Westerberg et al. | 5/421 X |
| 2,800,897 * | 7/1957 | Ross | 5/421 X |
| 2,833,276 * | 5/1958 | Murphy | 5/915 X |
| 2,902,993 * | 9/1959 | Wagner | 5/915 X |
| 2,939,454 * | 6/1960 | Lichtenstein et al. | 5/421 X |
| 2,943,620 * | 7/1960 | Sibert | 5/421 X |
| 2,943,621 * | 7/1960 | Phillips et al. | 5/915 X |
| 3,103,219 * | 9/1963 | Chadner | 5/421 X |
| 3,290,703 * | 12/1966 | Worrall | 5/490 X |
| 3,423,774 * | 1/1969 | Streetman | 5/490 |
| 3,480,760 * | 11/1969 | Young | 5/636 X |
| 3,981,032 * | 9/1976 | Brooks | 5/639 |
| 4,864,669 * | 9/1989 | Jones | 5/636 |
| 5,084,928 * | 2/1992 | Skillington | 5/490 |
| 5,099,533 * | 3/1992 | Bland | 5/490 |
| 5,361,437 * | 11/1994 | Zhu et al. | 5/639 |
| 5,462,515 * | 10/1995 | Tseng | 5/915 X |
| 5,727,266 * | 3/1998 | Pang | 5/490 |
| 5,836,900 * | 11/1998 | Leventhal | 5/915 X |
| 5,991,945 * | 11/1999 | Pang | 5/490 |
| 6,050,265 * | 4/2000 | Richardson | 5/636 X |
| 6,109,256 * | 8/2000 | Sardi | 5/421 X |

FOREIGN PATENT DOCUMENTS

| | | | |
|---|---|---|---|
| 2170100 * | 7/1986 | (GB) | 5/421 |
| 2274392 * | 7/1994 | (GB) | 5/915 |

* cited by examiner

*Primary Examiner*—Michael F. Trettel
*Assistant Examiner*—Robert G. Santos

(57) ABSTRACT

A heated massage pillow for allowing the massage packs to be removed and for keeping hair looking nice. The heated massage pillow includes a pillow. The pillow is comprised of a first pillow case and a foam rubber cushion. The foam rubber contains a heating means. A power supply means, adapted to fit inside the first pillow case adjacent to the foam rubber, is operationally coupled to the heating means. Vibrating means are adapted to fit inside the first pillow case adjacent to the power supply. The vibrating means are operationally coupled to the power supply means. An actuating means, located outside of said first pillow, is operationally attached to the vibrating means. The actuating means is adapted to activate the vibrating means and the heating means. A second pillow case of satin is adapted to fit over the first pillow case.

10 Claims, 3 Drawing Sheets

HEATED MASSAGE PILLOW

BACKGROUND OF THE INVENTION

1. Field of the Invention

The present invention relates to massage pillows and more particularly pertains to a new heated massage pillow for allowing the massage packs to be removed and for keeping hair looking nice.

2. Description of the Prior Art

The use of massage pillows is known in the prior art. More specifically, massage pillows heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,325,151; U.S. Pat. No. 4,006,604; U.S. Pat. No. 2,913,833; U.S. Pat. No. 3,648,469; U.S. Pat. No. 5,344,437; and U.S. Pat. No. Des. 282,515.

While these devices fulfill their respective, particular objectives and requirements, the aforementioned patents do not disclose a new heated massage pillow. The inventive device includes a pillow. The pillow is comprised of a first pillow case and a foam rubber cushion. The foam rubber contains a heating means. A power supply means, adapted to fit inside the first pillow case adjacent to the foam rubber, is operationally coupled to the heating means. Vibrating means are adapted to fit inside the first pillow case adjacent to the power supply. The vibrating means are operationally coupled to the power supply means. An actuating means, located outside of said first pillow, is operationally attached to the vibrating means. The actuating means is adapted to activate the vibrating means and the heating means. A second pillow case of satin is adapted to fit over the first pillow case.

In these respects, the heated massage pillow according to the present invention substantially departs from the conventional concepts and designs of the prior art, and in so doing provides an apparatus primarily developed for the purpose of allowing the massage packs to be removed and for keeping hair looking nice.

SUMMARY OF THE INVENTION

In view of the foregoing disadvantages inherent in the known types of massage pillows now present in the prior art, the present invention provides a new heated massage pillow construction wherein the same can be utilized for allowing the massage packs to be removed and for keeping hair looking nice.

The general purpose of the present invention, which will be described subsequently in greater detail, is to provide a new heated massage pillow apparatus and method which has many of the advantages of the massage pillows mentioned heretofore and many novel features that result in a new heated massage pillow which is not anticipated, rendered obvious, suggested, or even implied by any of the prior art massage pillows, either alone or in any combination thereof.

To attain this, the present invention generally comprises a pillow. The pillow is comprised of a first pillow case and a foam rubber cushion. The foam rubber contains a heating means. A power supply means, adapted to fit inside the first pillow case adjacent to the foam rubber, is operationally coupled to the heating means. Vibrating means are adapted to fit inside the first pillow case adjacent to the power supply. The vibrating means are operationally coupled to the power supply means. An actuating means, located outside of said first pillow, is operationally attached to the vibrating means. The actuating means is adapted to activate the vibrating means and the heating means. A second pillow case of satin is adapted to fit over the first pillow case.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new heated massage pillow apparatus and method which has many of the advantages of the massage pillows mentioned heretofore and many novel features that result in a new heated massage pillow which is not anticipated, rendered obvious, suggested, or even implied by any of the prior art massage pillows, either alone or in any combination thereof.

It is another object of the present invention to provide a new heated massage pillow which may be easily and efficiently manufactured and marketed.

It is a further object of the present invention to provide a new heated massage pillow which is of a durable and reliable construction.

An even further object of the present invention is to provide a new heated massage pillow which is susceptible of a low cost of manufacture with regard to both materials and labor, and which accordingly is then susceptible of low prices of sale to the consuming public, thereby making such heated massage pillow economically available to the buying public.

Still yet another object of the present invention is to provide a new heated massage pillow which provides in the apparatuses and methods of the prior art some of the advantages thereof, while simultaneously overcoming some of the disadvantages normally associated therewith.

Still another object of the present invention is to provide a new heated massage pillow for allowing the heating pack to be removed and for keeping hair looking nice. Should the user only wish to have the massage pack in the pillow, or if they would want to use the heating pack somewhere else, they may.

Yet another object of the present invention is to provide a new heated massage pillow which includes a satin cover. The satin cover allows the hair of the user to slide across the pillow with ease. Cotton and other cloths tend to pull on the hair which causes the hair to dry out and fray as well as become disheveled.

Still yet another object of the present invention is to provide a new heated massage pillow that allows the user to remove the massaging apparatus for use outside of the pillow.

These together with other objects of the invention, along with the various features of novelty which characterize the invention, arc pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
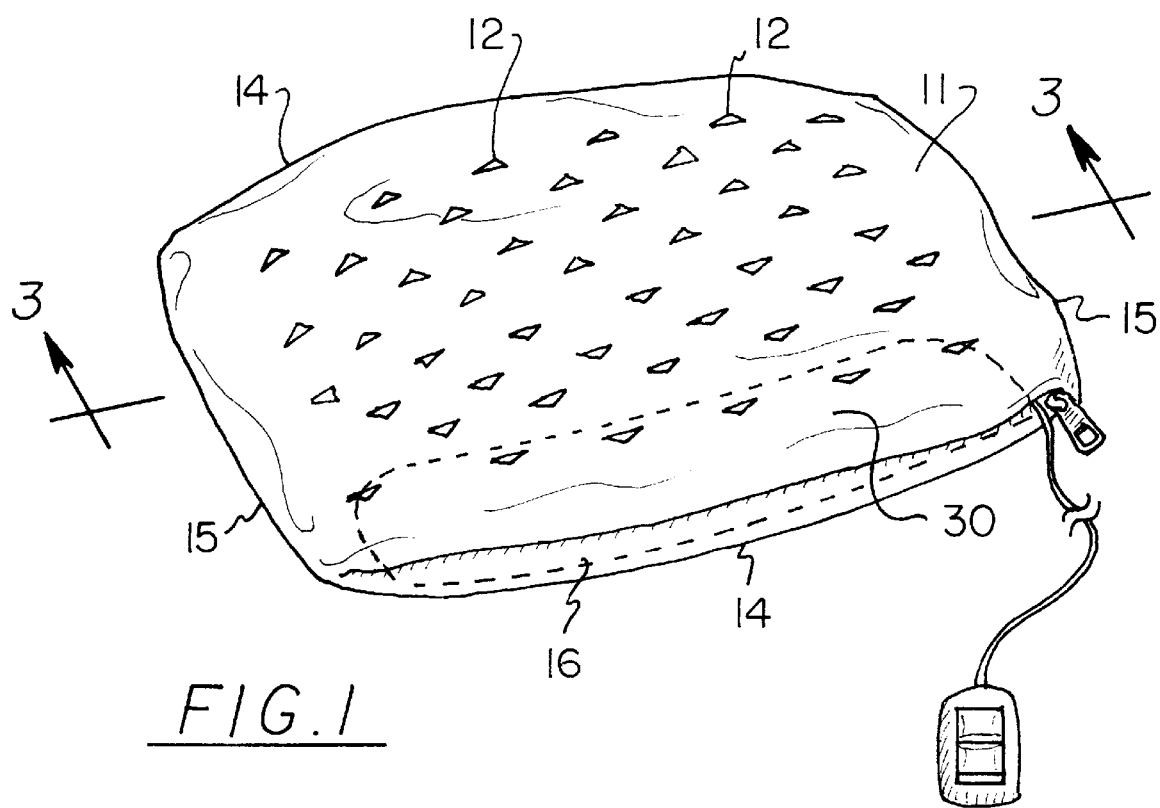
FIG. 1 is a schematic perspective view of a new heated massage pillow according to the present invention.
Figure 2:
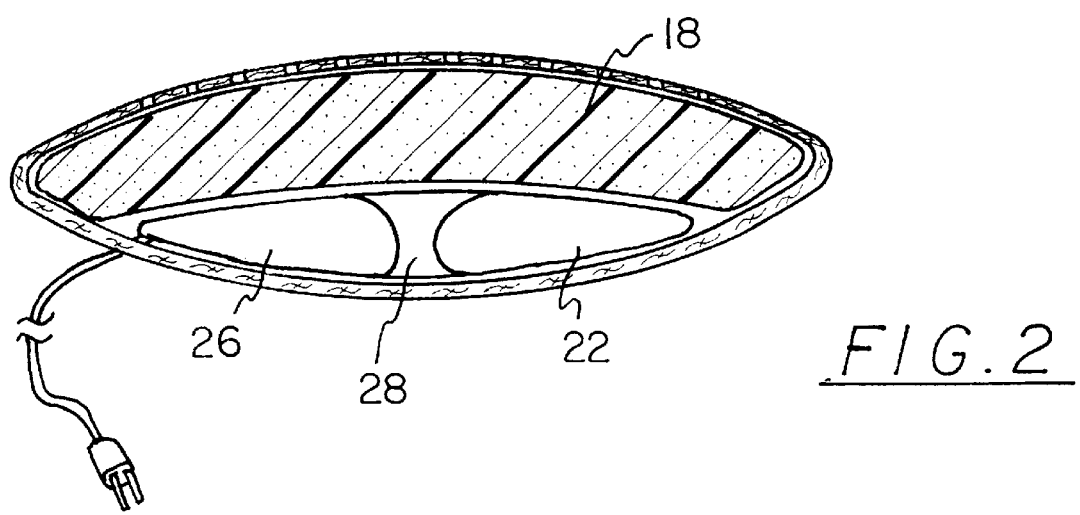
FIG. 2 is a schematic cross-sectional view of the present invention.
Figure 3:
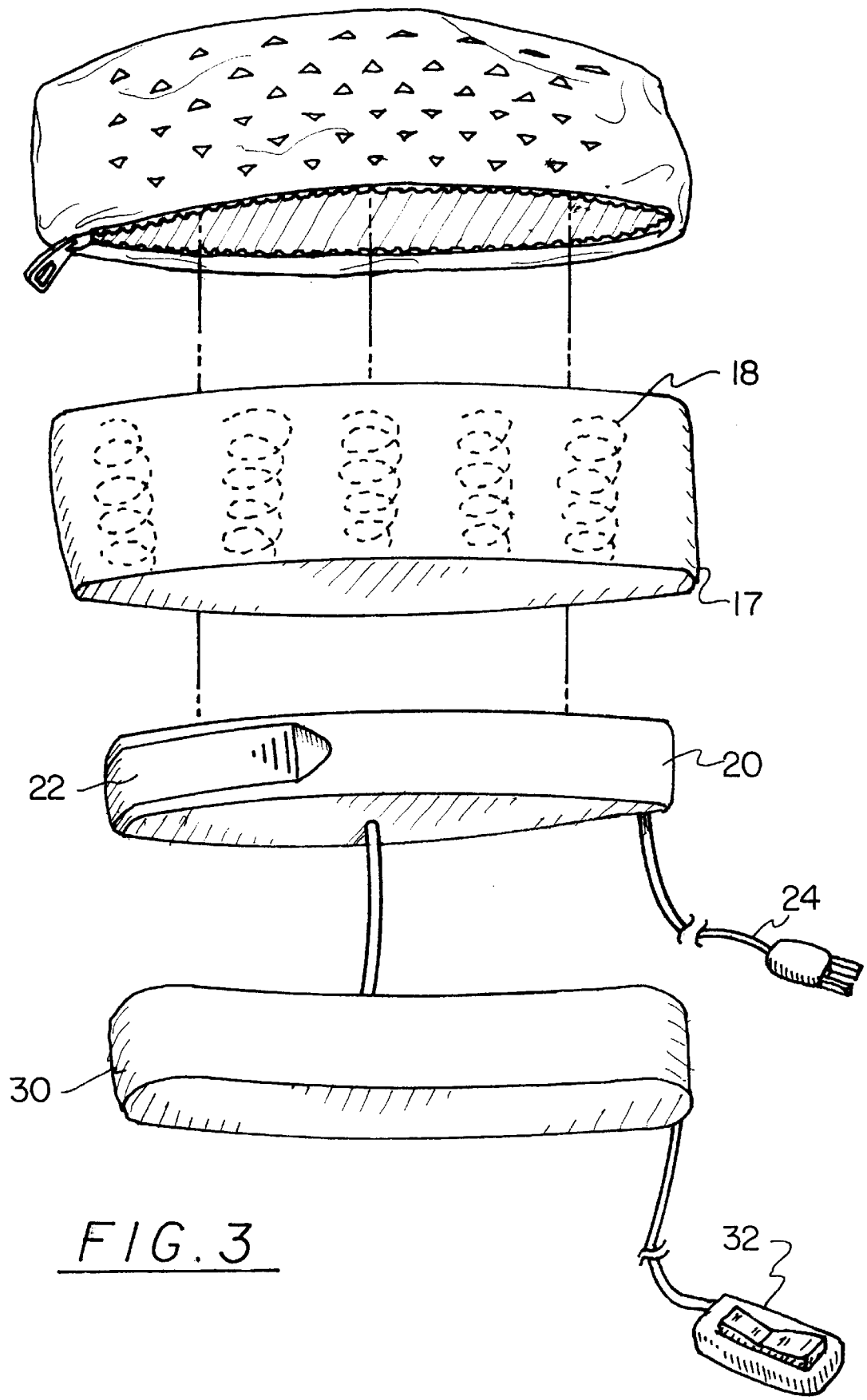
FIG. 3 is a schematic perspective cut-away view along line 3—3 of the present invention.
Figure 4:
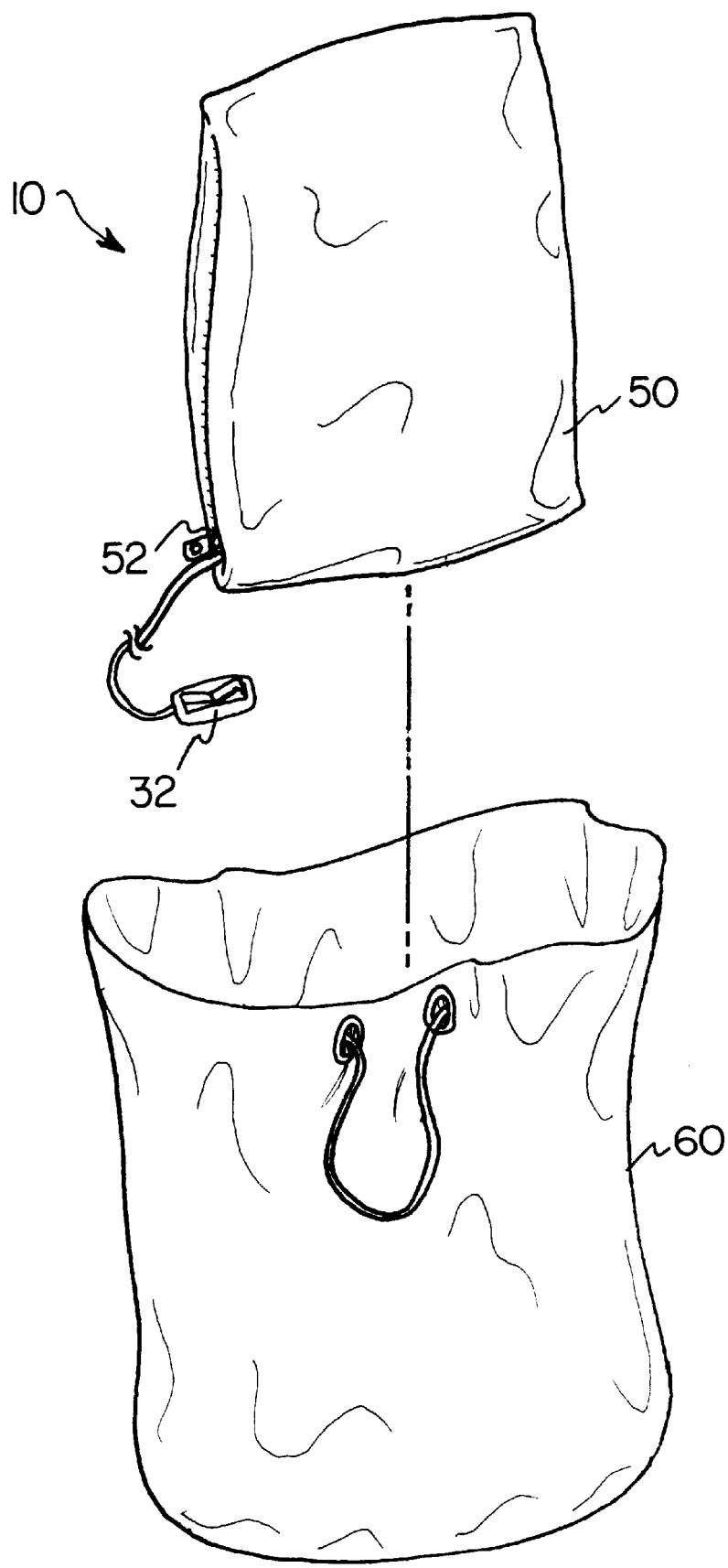
FIG. 4 is a schematic perspective view of a carrying bag for the present invention.

With reference now to the drawings, and in particular to FIGS. 1 through 4 thereof, a new heated massage pillow embodying the principles and concepts of the present invention and generally designated by the reference numeral 10 will be described.

As best illustrated in FIGS. 1 through 4, the heated massage pillow 10 generally comprises a pillow. The pillow is comprised of a first pillow case 11 with a plurality of perforations 12 therein. The perforations allow better circulation of air through the pillow. The pillow case has two elongate sides 14 and two short sides 15 where one of the elongate sides forms an opening and preferably has a zipper means 16 therein for closing the pillow case. Foam rubber is preferably used as the cushion 17 in the pillow. Preferably, the foam rubber contains a heating, means. Preferably the heating means is comprised of heating coils 18 The foam rubber is placed inside of the pillow case 11.

A power supply means 20, containing a battery 22, has a cord 24 attached to it. Preferably the power supply is adapted for AC power 26 for times when an outlet is nearby. The power supply means is removably coupled to the heating means (not shown). The power supply means is adapted to fit inside the first pillow case adjacent to the foam rubber. Preferably the power supply 28 is placed underneath and adjacent to the foam rubber 18.

A vibrating means 30 is operationally coupled to the power supply means. The vibrating means is adapted to fit inside the first pillow case adjacent to the power supply. Preferably, the vibrating means will rest near the zipper of the first pillow case in such a position as to massage the neck of the user.

An actuating means 32 is located outside of the first pillow case and is operationally coupled to the vibrating means. The actuating means is adapted to activate the vibrating means and the heating means. Preferably, the actuating means has variable settings to allow the user to adjust the heat and the vibrational intensity.

A second pillow case 50 is adapted to fit over the first pillow case. The second pillow case has two elongate sides and two short sides. One of the elongate sides has a zipper means 52 therein. Preferably the second pillow case is made from satin. Satin is very smooth and slippery allowing the hair of the user to glide along it. Other materials such as silk and rayon may also be used, however satin is the preferred material.

Preferably, a bag 60 for enclosing the pillow is used for carrying the apparatus on trips or anywhere the user would like to bring the pillow.

In use, the user places the foam rubber 17 in the first pillow case. Next they place the power supply 20 under the foam and attach the power supply to the heating coils 18 which are in the foam rubber. The massage unit, or vibrating means 30 is placed in the case next. The case is zipped up with the actuating means 32 hanging outside of the case. The second pillow case is placed over the first pillow case and zipped up with the actuating means hanging outside of the second pillow case. The second pillow, being made of satin, ensures the users hair will remain in orderly fashion. If the user is using battery power, they simply turn on the apparatus, if they are not using the battery, they plug the power supply into a power source such as an outlet. The user, if they choose, may remove the massage unit for use outside of the pillow.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A pillow system comprising:
   a pillow case having pair of opposite upper and lower panels defining an interior of said pillow case;
   a compressible pillow member formed of a foamed material, said pillow member being removably positioned in the interior of said pillow case in a location adjacent to the upper panel of the said pillow case for cushioning a head of a user rested on the upper panel of said pillow case;

a heating means positioned in said compressible pillow member for warming the upper panel of said pillow case;

a vibrating means positioned in the interior of the pillow case and located between said pillow member and the lower panel of said pillow case for vibrating said pillow member;

a power supply positioned in the interior of said pillow case and located between said pillow member and the lower panel of said pillow case such that said pillow member is adapted to cushion the head of the user resting on the upper panel from said power supply, said power supply being coupled to said heating means for supplying power to said heating means, said power supply being coupled to said vibrating means for supplying power to said vibrating means, and a control for controlling operation of said vibrating means and said heating means.

2. The pillow system of claim 1 wherein said upper panel of said pillow case has a plurality of perforations therethrough.

3. The pillow system of claim 1 wherein said pillow case has two elongate sides and two short sides, one of said elongate sides having a zipper mounted thereon for selectively closing an opening in said side of said pillow case.

4. The pillow system of claim 1 wherein said power supply includes a battery.

5. The pillow system of claim 1 wherein said power supply has a cord attached thereto for selectively connecting to an electrical outlet.

6. The pillow system of claim 1 wherein said heating means is comprised of a plurality of heating coils in said pillow member.

7. The pillow system of claim 1 additionally comprising a second pillow case, said second pillow case being adapted to fit over said first pillow case, said second pillow case being formed of a satin material.

8. The pillow system of claim 1 wherein the pillow member has a length and the power supply has a length, and wherein the length of the pillow member is greater than the length of the power supply such that ends of said pillow member extend beyond ends of said power supply in said pillow case.

9. The pillow system of claim 1 wherein each of the pillow member, the power supply, and the vibrating means has a width, and the width of the pillow member is approximately twice the widths of the power supply and the vibrating means such that said pillow member is able to cover said power supply and said vibrating means in said pillow case.

10. The pillow system of claim 1 additionally comprising a second pillow case, said second pillow case being adapted to fit over said first pillow case, said second pillow case being formed of a satin material;

wherein the pillow member has a length and the power supply has a length, and wherein the length of the pillow member is greater than the length of the power supply such that ends of said pillow member extend beyond ends of said power supply in said pillow case;

wherein each of the pillow member, the power supply, and the vibrating means has a width, and the width of the pillow member is approximately twice the widths of the power supply and the vibrating means such that said pillow member is able to cover said power supply and said vibrating means in said pillow case;

wherein said upper panel of said pillow case has a plurality of perforations therethrough;

wherein said pillow case has two elongate sides and two short sides, one of said elongate sides having a zipper mounted thereon for selectively closing an opening in said side of said pillow case;

wherein said power supply includes a battery;

wherein said power supply has a cord attached thereto for selectively connecting to an electrical outlet; and wherein said heating means is comprised of a plurality of heating coils in said pillow member.

* * * * *